United States Patent [19]

Hope et al.

[11] 4,309,337
[45] Jan. 5, 1982

[54] NOVEL ORGANOTIN COMPOUNDS, A PROCESS FOR THEIR PREPARATION AND THEIR USE AS STABILIZERS FOR POLYVINYL CHLORIDE POLYMERS

[75] Inventors: Peter Hope, Formby; Malcolm Mellor, St. Helens, both of England

[73] Assignee: Akzo N.V., Arnhem, Netherlands

[21] Appl. No.: 100,962

[22] Filed: Dec. 6, 1979

[30] Foreign Application Priority Data

Dec. 7, 1978 [GB] United Kingdom ............... 47643/78

[51] Int. Cl.$^3$ ............................ C08K 5/58; C07F 7/22
[52] U.S. Cl. .............................. 260/45.75 S; 260/429.7
[58] Field of Search ........................ 260/429.7, 45.75 S

[56] References Cited

U.S. PATENT DOCUMENTS

| | | | |
|---|---|---|---|
| 2,704,756 | 3/1955 | Leistner et al. | 260/45.75 S X |
| 2,731,482 | 1/1956 | Stefl | 260/45.75 S X |
| 2,891,922 | 6/1959 | Johnson | 260/45.75 S X |
| 3,413,222 | 0/1968 | Hoffen | 252/351 |
| 3,793,356 | 2/1974 | Williams | 260/429.7 |
| 3,931,262 | 1/1976 | Wirth et al. | 260/429.7 |
| 3,957,598 | 0/1976 | Merkl | 204/72 |
| 4,043,957 | 8/1977 | Szabo | 260/45.75 S X |
| 4,134,878 | 1/1979 | Burley et al. | 260/429.7 X |

FOREIGN PATENT DOCUMENTS 887945 of 1953 Fed. Rep. of Germany.

*Primary Examiner*—Helen M. S. Sneed
*Attorney, Agent, or Firm*—Stevens, Davis, Miller & Mosher

[57] ABSTRACT

Novel organotin compounds of the formula:

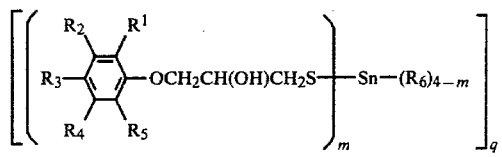

wherein q is 1 or 2; m is 1,2 or 3; $R_6$ is an alkyl group having from 1 to 18 carbon atoms, a cycloalkyl group having from 3 to 6 carbon atoms, an aryl group, an aralkyl group, and alkaryl group having up to 30 carbon atoms, or a group of the formula:

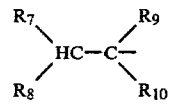

wherein $R_7$, $R_8$, $R_9$ and $R_{10}$ are each independently an alkyl group having from 1 to 18 carbon atoms, an oxygen-containing hydrocarbon group or a hydrogen atom, with the proviso that at least one of $R_7$ and $R_8$ contains, adjacent to the HC grouping, a carbonyl group which forms part of an acid group, an ester group, and acid halide group, a ketone group or an aldehyde group; when q=1, $R_1$, $R_2$, $R_3$, $R_4$ and $R_5$, are each independently, a hydrogen atom, an alkyl or alkoxy group having from 1 to 14 carbon atoms, a cycloalkyl or cycloalkoxy group, having from 3 to 6 carbon atoms, a nitro group or a halogen atom; and when q=2, m=1, and the two structural units in the para position are interlinked directly or by way of an oxygen atom, a methylene group, an $SO_2$ group of an isopropylidene group and $R_1$, $R_2$ $R_4$ and $R_5$ are each as defined above, and a process for making the same.

The compounds may be formulated into stabilizer compositions and used to stabilize polyvinyl chlorides and polyvinylidene chloride against heat and light deterioration. They may be used with 2,4,6-trisubstituted phenolic antioxidants, and mono or di-alkyl or ester tin sulphides.

10 Claims, No Drawings

NOVEL ORGANOTIN COMPOUNDS, A PROCESS FOR THEIR PREPARATION AND THEIR USE AS STABILIZERS FOR POLYVINYL CHLORIDE POLYMERS

The present invention relates to novel organotin compounds, to their method of preparation, to stabilizer compositions containing one or more of these compounds and to vinyl chloride containing polymers or polymer compositions stabilized therewith, such as polyvinyl chloride, polyvinylidene chloride and copolymers thereof. A particular class of organotin stabilizers for polymers, particularly polyvinyl chloride and copolymers thereof, is described in Japanese Patent Publication No. 52-38556. These known organotin compounds are organotin mercapto compounds having at least one alkyl group capable of bonding to tetravalent tin and having 1 to 12 carbon atoms, and a hydroxymercaptan residue expressed by the general formula:

$$-S-CH_2-CH-R$$
$$\phantom{-S-CH_2-C}|$$
$$\phantom{-S-CH_2-CH}OH$$

where R is an alkyl or an alkoxyalkyl group having from 6 to 26 carbon atoms.

These organotin compounds are claimed to be especially suitable for stabilizing vinyl chloride based polymers against deterioration by heat and light.

It has now been found that the heat and light stability of vinyl chloride based polymers or polymer compositions can be enhanced considerably by the incorporation of organotin mercapto compounds of the formula:

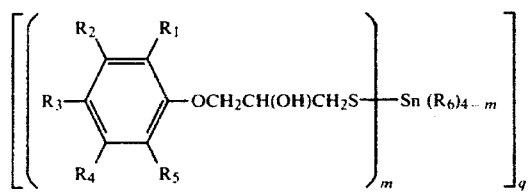

wherein q is 1 or 2, m is 1, 2 or 3; $R_6$ is an alkyl group having from 1 to 18 carbon atoms, a cycloalkyl group having from 3 to 6 carbon atoms, an aryl group, an aralkyl group, an alkaryl group having up to 30 carbon atoms, or a group of the formula:

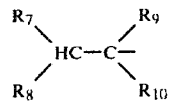

wherein $R_7$, $R_8$, $R_9$ and $R_{10}$ are each independently an alkyl group having from 1 to 18 carbon atoms, an oxygen-containing hydrocarbon group or a hydrogen atom, with the proviso that at least one of $R_7$ and $R_8$ contains, adjacent to the HC grouping, a carbonyl group which forms part of an acid group, an ester group, an acid halide group, a ketone group or an aldehyde group; when q=1, $R_1$, $R_2$, $R_3$, $R_4$ and $R_5$, are, each independently, a hydrogen atom, an alkyl or alkoxy group having from 1 to 14 carbon atoms, a cycloalkyl or cycloalkoxy group, having from 3 to 6 carbon atoms, a nitro group or a halogen atom, and when q=2, m=1, and the two structural units in the para position are interlinked, directly or by way of an oxygen atom, a methylene group, an $SO_2$ group or an isopropylidene group, and $R_1$, $R_2$, $R_4$ and $R_5$ are each as defined above.

According to a preferred embodiment of the present invention, there are provided novel organotin compounds according to the above formula wherein $R_6 = R_{11}$ $OCOCH_2$ $CH_2-$, $R_{11}$ being an alkyl group having from 1 to 18 carbon atoms. The compounds may conveniently be prepared by reacting, at a temperature of from 10° to 180° C., a compound having the formula:

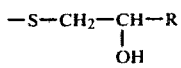

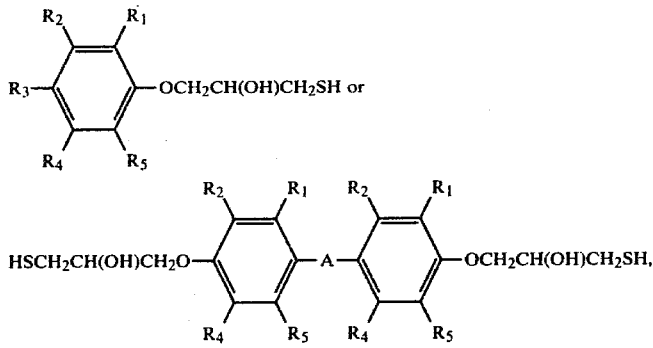

wherein $R_1$, $R_2$, $R_3$, $R_4$ and $R_5$ are as defined above and A represents a direct link or an oxygen atom, a methylene group, an $SO_2$ group or an isopropylidene group, with an organotin oxide or chloride having at least one $R_6$ group as hereinbefore defined and isolating the reaction product obtained. The compounds of the invention are especially suitable for the stabilization against heat-deterioration of vinyl chloride based polymers or polymer-compositions, such as polyvinyl chloride, polyvinylidene chloride and copolymers thereof subjected to extremely severe and unusual conditions of temperature and mechanical working during extrusion and calendering operations. Accordingly it is an object of this invention to provide a stabilizer composition adapted to counteract the deteriorative effect of heat on vinyl chloride based polymers comprising a stabilising amount of an organotin compound as defined above.

In a further aspect the present invention provides a stabilizer composition which comprises a synergistic combination of two organotin compounds according to the first mentioned formula, wherein one organotin compound has the structure $R_6Sn$ $(MAP)_3$ and the other one $(R_6)_2Sn(MAP)_2$, wherein MAP refers to the group

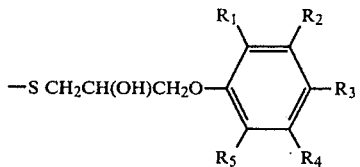

wherein $R_1$, $R_2$, $R_3$, $R_4$, $R_5$ and $R_6$ are each as defined above.

In a preferred embodiment of the present invention the meaning of $R_6$ in the last mentioned synergistic combination of organotin compounds is $R_{11}O\text{-}COCH_2CH_2\text{—}$, wherein $R_{11}$ is as defined above.

Exceptionally good results are obtained with a stabilizer composition comprising such a synergistic combination and from 5 to 15% by weight, based on the said synergistic combination, of a 2,4,6-trisubstituted phenolic antioxidant.

In yet a further aspect the present invention provides a stabilizer composition comprising an organotin compound according to the invention, preferably one having the structure $R_6Sn(MAP)_3$, wherein $R_6$ is a group of the formula $R_{11}OCOCH_2CH_2\text{—}$, and a synergistic amount of a monoalkyltin sulphide, a dialkyltin sulphide, a monoester tin sulphide, and/or a diester tin sulphide. The monoalkyltin sulphide is preferably monobutyltin sulphide. The ester group in the mono and diestertin sulphide preferably has the formula $R_{11}OCOCH_2CH_2\text{—}$, wherein $R_{11}$ is as defined above.

In a further aspect the present invention provides a polymer composition which comprises a vinyl chloride based polymer together with a stabilizer composition as defined above in an amount of from 0.1 to 5 percent by weight of the vinyl chloride based polymer.

In yet a further aspect the present invention provides a method of fabricating a polymer article in which the polymer is stabilized with a stabilizer composition of the present invention as defined above. The stabilizer compositions of the present invention are particularly suitable for improving the thermal stability of polyvinyl chloride resins of all types, by whatever process they are prepared, for instance, by solution polymerization, emulsion polymerization and suspension polymerization, to name only a few.

The term "polyvinyl chloride" as used herein is inclusive not only for polyvinyl chloride homopolymers of all types, and of postchlorinated polyvinyl chloride, but also of copolymers of vinyl chloride in a major proportion, and other copolymerizable monomers in a minor proportion, such as copolymers of vinyl chloride and vinyl acetate, copolymers of vinyl chloride and vinylidene chloride, copolymers of vinyl chloride and acrylonitrile, copolymers of vinyl chloride with maleic acid or fumaric acid esters and copolymers of vinyl chloride with styrene, and also mixtures of polyvinyl chloride resins in a major proportion with a minor proportion of other synthetic resins, such as chlorinated polyethylene, or copolymers of acrylonitrile, butadiene and styrene.

The following examples demonstrate the improvements in stability of a vinyl chloride based polymer brought about by incorporation therein of the novel organotin stabilizers of the present invention, as well as the synergistic properties of one or more organotin compounds and a phenolic antioxidant.

In all the following Examples unless otherwise indicated the following standard polymer formulation was used:

|  | Parts by weight |
|---|---|
| A suspension P.V.C. of K value 68 | 100 |
| Stearate-coated calcium carbonate | 3 |
| Titanium dioxide pigment | 1 |
| Calcium stearate | 0.8 |
| Paraffin wax | 1.2 |
| Oxidized low-molecular weight polyethylene wax | 0.15 |
| Stabilizer (Total tin-containing components) | 0.3 |

The various ingredients were mixed in each case in a 3-liter capacity Papenmeier high speed mixer at a maximum temperature of 100° C. The resulting mixtures were cooled to 50° C. before they were released.

The mixture obtained was used for making a 2,5 cm diameter pressure pipe on a Krauss Maffei KML-25 twin-screw extruder under the following standard conditions.

| Barrel zone 1 temperature | 200° C. |
|---|---|
| Barrel zone 2 temperature | 180° C. |
| Die zone 1 temperature | 190° C. |
| Die zone 2 (die tip) temperature | 200° C. |
| Screw temperature | 160° C. |
| Screw speed (r.p.m.) | 30 |

The above procedure was used with formulations differing from each other in the type of tin stabilizer used. Test specimens of a pipe of each formulations were examined visually for rate of color development, which was taken as indicative of the rate of decomposition of the P.V.C.

Residual Oven Stability Test

In this test, each formulation was cut into 11 test specimens.

A test specimen was placed in each of 11 aluminium trays. The trays were then stacked in an air circulating oven at 185° C. and withdrawn at 10 minute intervals. On cooling a small specimen was punched out of each test piece and mounted on a card under a specimen of unaged pipe.

Press Test

Specimens of extruded pipe were cut out and pressed between two polished stainless steel plates at 180° C. in a steam-heated hydraulic press. The following procedure was used:

| Preheating with plates touching | 1 minute |
|---|---|
| Pressure 50 kilos per m² | 1 minute |
| Pressure 250 kilos per m² | 1,5,10,20 and 30 minutes |

After allowing the above specimens to cool while under full pressure samples were punched out of them and mounted on a card.

Dynamic Stability Test

Dynamic stability tests were carried out with samples of dry blend formulations used in the extrusion trials. For these evaluations a Brabender Plasticorder fitted with a 50 ml-capacity roller mixed head was used. The test conditions were as follows:

| Mixer head temperature | 200° C. |
|---|---|
| Rotor speed (r.p.m.) | 30 |
| Charge weight (g) | 63 |

The test was timed from charging. After 2 minutes the charging chute and ram were removed. A small chip of material was removed with a pair of needle pliers. This procedure was repeated at 2 minute intervals up to degradation, the chips being mounted on a card. For formulations with gelation times in excess of 2 minutes the first chip was taken after 4 minutes and mounted in the 4-minute position.

EXAMPLE I

Preparation of β-carbobutoxyethyl tin tris(1-mercapto-2-hydroxy 3-phenoxy propane). 150.0 g of 2-carbobutoxyethyltin trichloride was dissolved in 200 ml of toluene and 271.9 g of 1-mercapto-3-phenoxy-2-propanol (—SH content 16.18%) added. The mixture was stirred and 115.3 g of sodium hydrogen carbonate slowly added. Stirring was continued for sixteen hours at room temperature. The mixture was then filtered to remove sodium chloride and the filtrate stripped of toluene on a rotarory evaporator. The product was a viscous pale yellow liquid (yield 361.4 g). Analysis indicated 14.2% Sn, less than 0.01% Cl.

EXAMPLE II

In this example the following mono-β-carbobutoxyethyl tin compounds of the prior art were compared with a tin compound of the present invention.

| No. | Mono-β-carbobutoxyethyl tin derivative of | Formula of tin compound $R^1 = BuO_2C \cdot CH_2CH_2-$ |
|---|---|---|
| I | lauryl mercaptan | $R^1Sn(SC_{12}H_{25})_3$ |
| II | iso-octyl thioglycollate | $R^1Sn(SCH_2CO_2C_8H_{17})_3$ |
| III | 2-mercaptoethyl oleate | $R^1Sn(SCH_2CH_2O_2C\ C_{17}H_{33})$ |
| IV | 2-hydroxylauryl mercaptan | $R^1Sn(SCH_2CH(OH)C_{10}H_{21})_3$ |
| V | 1-mercapto-3-phenoxypropane | $R^1Sn(SCH_2CH_2CH_2O\ C_6H_5)_3$ |
| VI | 1-mercapto-3-phenyl-2-propanol | $R^1Sn(SCH_2CH(OH)CH_2C_6H_5)_3$ |
| VII | 1-mercapto-3-octoxy-2-propanol | $R^1Sn(SCH_2CH(OH)CH_2OC_8H_{17})_3$ |
| VIII | 1-mercapto-3-phenoxy-2-propanol (invention) | $R^1Sn(SCH_2CH(OH)CH_2OC_6H_5)_3$ |

The formulation of the PVC used was as follows:

|  | Parts by weight |
|---|---|
| PVC-suspension polymer of K value 65–67 | 100 |
| titanium dioxide pigment | 1 |
| stearate-coated calcium carbonate | 3 |
| paraffin wax | 1.2 |
| calcium stearate | 0.8 |
| oxidized polyethylene wax | 0.15 |
| 2,4,6-trisubstituted phenol | 0.03 |

The various tin compounds were incorporated at equal tin level as shown below:
Of each composition 63 g were gelled in a Brabender torque rheometer. The temperature of the head was maintained at 200° C. with a rotational speed of 30 revolutions per minute.

Samples were withdrawn from the melt at 2 minute intervals until decomposition occurred. Their colours were assessed on a scale from 1 (white) to 10 (dark grey):

TABLE 1

| Tin Compound | Minutes after charging | | | | |
|---|---|---|---|---|---|
|  | 2 | 4 | 6 | 8 | 10 |
| 0.3 p.h.r. I | 3 | 4 | 4 | 7 |  |
| 0.3 p.h.r. II | 1 | 3 | 5 | 7 | 9 |
| 0.55 p.h.r. III | 2 | 3 | 4 | 7 |  |
| 0.32 p.h.r. IV | 2 | 2 | 6 | 7 |  |
| 0.27 p.h.r. V | 3 | 3 | 6 | 7 |  |
| 0.33 p.h.r. VI | 2 | 2 | 6 | 7 | 9 |
| 0.37 p.h.r. VII | 2 | 3 | 5 | 7 |  |
| 0.31 p.h.r. VIII (invention) | 1 | 1 | 3 | 7 | 9 |

Samples of the same PVC compositions were also mixed on a two-roll mill at 170° C. for five minutes after gelation. Portions of the gelled compound were then pressed between polished steel plates at 170° C. for one minute (light contact) followed by one or ten minutes under pressure. The resulting PVC plaques were assessed for colour on the scale from 1–10:

TABLE 2

| Tin Compound | Press Time | |
|---|---|---|
|  | 1 Minute | 10 Minutes |
| 0.3 p.h.r. I | 4 | 4 |
| 0.3 p.h.r. II | 3 | 3 |
| 0.55 p.h.r. III | 3 | 3 |
| 0.32 p.h.r. IV | 2 | 2 |
| 0.27 p.h.r. V | 4 | 4 |
| 0.33 p.h.r. VI | 2 | 2 |
| 0.37 p.h.r. VII | 3 | 4 |
| 0.31 p.h.r. VIII (invention) | 1 | 2 |

These results demonstrate that the tin compounds derived from 1-mercapto-3-phenoxy-2-propanol gives the best early colour and colour hold. Analogous compounds lacking the 2-hydroxy or 3-phenoxy-structures do not perform as well.

EXAMPLE III

In this example the standard P.V.C. formulation as indicated above was used, except that the amount of stabilizer per 100 parts of P.V.C. was 0.4 parts instead of 0.3 parts.

A Brabender Plastograph was used for carrying out a dynamic Stability Test.

The times when the first colour appeared and the times when degradation started are indicated in Table 3.

TABLE 3

| No | Stabilizer | Time 1st color (minutes) | Time to degradation (minutes) |
|---|---|---|---|
| 1 | $\left(\langle\bigcirc\rangle\text{—O—CH}_2\text{CH(OH)CH}_2\text{S—}\right)_3\text{SnCH}_2\text{CH}_2\overset{\text{O}}{\overset{\|}{\text{C}}}\text{—OC}_4\text{H}_9$ | 11 | 14 |
| 2 | $\left(\text{C}_9\text{H}_{19}\text{—}\langle\bigcirc\rangle\text{—OCH}_2\text{CH(OH)CH}_2\text{S—}\right)_3\text{SnCH}_2\text{CH}_2\overset{\text{O}}{\overset{\|}{\text{C}}}\text{OC}_4\text{H}_9$ | 8 | 14 |
| 3 | $\left(\langle\bigcirc\rangle\text{—OCH}_2\text{CH(OH)CH}_2\text{S—}\right)_3\text{SnC}_4\text{H}_9$ | 10 | >18 |
| 4 | $(\text{C}_{12}\text{H}_{25}\text{S})_3\text{SnCH}_2\text{CH}_2\overset{\text{O}}{\overset{\|}{\text{C}}}\text{OC}_4\text{H}_9$ | starts cream | 15 |
| 5 | $(\text{C}_{12}\text{H}_{25}\text{S})_3\text{Sn C}_4\text{H}_9$ | starts cream | 17 |
| 6 | $(\text{C}_{10}\text{H}_{21}\text{CH(OH)CH}_2\text{—S})_3\text{SnCH}_2\text{CH}_2\overset{\text{O}}{\overset{\|}{\text{C}}}\text{OC}_4\text{H}_9$ | 7 | 11 |

Compounds no. 1, 2 and 3 in the above table are according to the invention. Compounds 4 and 5 are prior art compounds, and compound 6 is an estertin similar to the alkyltin compounds disclosed in Japanese Patent Publication No. 52-38556.

EXAMPLE IV

In this example the standard P.V.C. formulation was used, and the organotin compounds according to the invention were as follows:

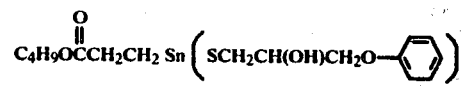

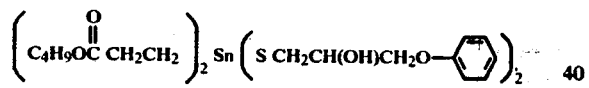

The first compound is β-carbobutoxyethyl tin tris(1-mercapto-2-hydroxy-3-phenoxy propane) and will be referred to as BuAcSn (MPP)₃ and the second compound is di-(β-carbobutoxyethyl) tin bis(1-mercapto-2-hydroxy-3-phenoxy propane) and will be referred to as (BuAc)₂Sn(MPP)₂. Stabilizer compositions were prepared using these compounds.

The stabilizer compositions also contained a 2,4,6-trisubstituted phenolic antioxidant. The compositions were as shown in Table 4, which also includes a commercial butylthiotin stabilizer.

TABLE 4

| Stabilizer composition No. | 7 | 8 | 9 | 10 | 11 | 12 |
|---|---|---|---|---|---|---|
| stabilizer compound | | | weight percent of stabilizer | | | |
| commercial butylthiotin stabilizer | 100 | — | — | — | — | — |
| BuAcSn (MPP)₃ | — | 90 | 70 | 45 | 20 | — |
| (BuAc)₂Sn(MPP)₂ | — | — | 20 | 45 | 70 | 90 |
| phenolic antioxidant | — | 10 | 10 | 10 | 10 | 10 |

Each of the stabilizer compositions was used in the standard P.V.C. compositions given above, and each composition was treated in an oven.

The results of the oven test at 185° C. are given in Table 5. The colour development is measured on the following scale:

TABLE 5

| 1 → 8: | very white → | pale yellow |
|---|---|---|
| 9 → 12: | yellow → | light tan |
| 13 → 18: | light green → | dark green |

Colour developed after a given time interval at 185° C.

| stabilizer composition | 0 | 10 | 20 | 30 | 40 | 50 | 60 | 70 | 80 | 90 |
|---|---|---|---|---|---|---|---|---|---|---|
| 7 | 3 | 3 | 3 | 3 | 8 | 12 | 13 | 14 | 14 | 14 |
| 8 | 1 | 1 | 1 | 1 | 6 | 8 | 14 | 16 | 18 | 18 |
| 9 | 2 | 2 | 2 | 2 | 7 | 9 | 14 | 16 | 18 | 18 |
| 10 | 3 | 3 | 3 | 3 | 8 | 8 | 9 | 15 | 17 | 18 |
| 11 | 4 | 4 | 4 | 7 | 8 | 8 | 9 | 9 | 14 | 17 |
| 12 | 5 | 6 | 7 | 8 | 9 | 10 | 11 | 12 | 13 | 13 |

It can be seen from Table 5 that a peak in the synergistic effect with about 10% of phenolic antioxidant is reached with approximately equal amounts of BuAcSn(MPP)₃ and (BuAc)₂Sn(MPP)₂.

EXAMPLE V

This example demonstrates that the stabilizing effect of

is enhanced considerably by the use of mono-butyltin sulphide (M.B.T.S.) Stabilizer compositions were prepared containing varying proportions of these compounds, as shown in Table 6, and compounds with commercially available butyl and methyl thiotin stabilizers.

The stabilizer compositions also contained a 2,4,6-trisubstituted phenolic antioxidant and a plasticizer (dioctyl phthalate).

TABLE 6

| composition No. | 7 | 13 | 14 | 15 | 16 | 17 | 18 | 19 |
|---|---|---|---|---|---|---|---|---|
| compound | | | weight percent of stabilizer compound | | | | | |
| commercial butyl thiotin stabilizer | 100 | — | — | — | — | — | — | — |
| commercial methyl thiotin stabilizer | — | 100 | — | — | — | — | — | — |
| Bu Ac Sn(MPP)$_3$ | — | — | 67,6 | 60,9 | 54,2 | 47,5 | 40,8 | 34,1 |
| M.B.T.S. | — | — | — | 2,0 | 4,0 | 6,0 | 8,0 | 10,0 |
| phenolic antioxidant | — | — | 10 | 10 | 10 | 10 | 10 | 10 |
| dioctylphthalate (D.O.P.) | — | — | 22,4 | 27,1 | 31,8 | 36,5 | 41,2 | 45,9 |

Each of the stabilizer compositions was used in the standard P.V.C. composition given above.

The results of the oven test at 185° C. are given in Table 7. The numbers in table 7 correspond to the following colour code:

TABLE 7

| 1 → 4: | very white → | pale yellow |
| 5 → 10: | yellow → | light tan |
| 11 → 14: | light green → | dark green |

| Composition No. | Colour developed after stated period at 185° C. minutes | | | | | | | | | |
|---|---|---|---|---|---|---|---|---|---|---|
| | 0 | 10 | 20 | 30 | 40 | 50 | 60 | 70 | 80 | 90 |
| 7 | 2 | 2 | 2 | 2 | 3 | 10 | 11 | 12 | 14 | 14 |
| 13 | 1 | 1 | 1 | 1 | 4 | 6 | 7 | 8 | 10 | 14 |
| 14 | 2 | 2 | 2 | 2 | 3 | 5 | 7 | 9 | 14 | 14 |
| 15 | 1 | 1 | 1 | 1 | 3 | 5 | 7 | 9 | 13 | 14 |
| 16 | 1 | 1 | 1 | 1 | 2 | 6 | 7 | 9 | 13 | 14 |
| 17 | 1 | 1 | 1 | 1 | 1 | 7 | 7 | 9 | 13 | 14 |
| 18 | 1 | 1 | 1 | 1 | 1 | 7 | 7 | 9 | 13 | 14 |
| 19 | 1 | 1 | 1 | 2 | 4 | 8 | 8 | 9 | 14 | 14 |

It can be seen from Table 7 that a synergistic effect is reached here with approximately from 3 to 20 percent by weight M.B.T.S. calculated on the amount of BuAcSn(MPP)$_3$.

EXAMPLE VI

This example demonstrates that the performance of (BuAc)$_2$ Sn (MPP)$_2$ (at 10% Sn level) is enhanced considerably by the addition of mono-butyl tin sulphide.

Stabilizer compositions were prepared as shown in Table 8. The stabilizer formulations also contained a phenolic antioxidant and a plasticizer (dioctyl phthalate).

TABLE 8

| Composition No. | 7 | 13 | 20 | 21 | 22 | 23 | 24 | 25 |
|---|---|---|---|---|---|---|---|---|
| compound | | | weight percent of stabilizer compound | | | | | |
| commercial butyl thio tin stabilizer | 100 | — | — | — | — | — | — | — |
| commercial methyl thio tin stabilizer | — | 100 | — | — | — | — | — | — |
| (BuAc)$_2$Sn(MPP)$_2$ | — | — | 63 | 57,5 | 50,7 | 44,4 | 38,2 | 31,9 |
| M.B.T.S. | — | — | — | 2,0 | 4,0 | 6,0 | 8,0 | 10,0 |
| phenolic antioxidant | — | — | 10,0 | 10,0 | 10,0 | 10,0 | 10,0 | 10,0 |
| DOP | — | — | 27,0 | 31,0 | 35,3 | 39,6 | 43,8 | 48,1 |

Each stabilizer composition was used with the standard P.V.C. composition. The results of oven tests on the various P.V.C. compositions are given in Table 9. The numbers in table 9 correspond to the following colour code:

TABLE 9

| 1 → 3: | white → | cream |
| 4 → 8: | pale yellow → | tan |
| 9 → 12: | light green → | dark green |

| Composition No. | Colour developed after stated period at 185° C. minutes | | | | | | | | | |
|---|---|---|---|---|---|---|---|---|---|---|
| | 0 | 10 | 20 | 30 | 40 | 50 | 60 | 70 | 80 | 90 |
| 7 | 2 | 2 | 2 | 3 | 8 | 9 | 9 | 10 | 11 | 12 |
| 13 | 1 | 1 | 1 | 3 | 4 | 5 | 8 | 10 | 11 | 12 |
| 20 | 2 | 2 | 2 | 3 | 4 | 7 | 7 | 8 | 9 | 10 |
| 21 | 1 | 1 | 1 | 2 | 4 | 5 | 7 | 8 | 9 | 10 |
| 22 | 1 | 1 | 1 | 1 | 3 | 5 | 7 | 8 | 9 | 10 |
| 23 | 1 | 1 | 1 | 1 | 2 | 5 | 7 | 8 | 9 | 10 |
| 24 | 1 | 1 | 1 | 1 | 1 | 5 | 7 | 8 | 9 | 10 |
| 25 | 1 | 1 | 1 | 1 | 1 | 5 | 6 | 8 | 9 | 10 |

EXAMPLE VII

The same procedure was used as in Example VI, except that the mono butyl tin sulphide was replaced by a mixture of mono- and diestertin sulphides.

Stabilizer compositions were made up as follows:

TABLE 10

| Composition No. | 7 | 13 | 26 | 27 | 28 | 29 |
|---|---|---|---|---|---|---|
| compound | | | weight percent of stabilizer compound | | | |
| commercial butyl thiotin stabilizer | 100 | — | — | — | — | — |
| commercial methyl thiotin stabilizer | — | 100 | — | — | — | — |
| equal parts by weight of BuAcSn(MPP)$_3$ and (BuAc)$_2$Sn(MPP)$_2$ | — | — | 67,6 | 50,8 | 50,8 | 50,8 |
| BuAcSn$_{3/2}$ + | — | — | — | — | 5,0 | — |
| Oct AcSn$_{3/2}$ × | — | — | — | — | — | 5,1 |
| M.B.T.S. | — | — | — | 5,0 | — | — |
| phenolic antioxidants | — | — | 10,0 | 10,0 | 10,0 | 10,0 |
| DOP | — | — | 24,4 | 34,2 | 34,2 | 34,0 |

BuAcSnS$_{3/2}$ + refers to β-carbobutoxyethyl tin sulphide
Oct AcSn$_{3/2}$ × refers to β-carbo-2-ethylhexoxyethyl tin sulphide The results of the oven test at 185° C. are given in Table 11. The numbers in said table correspond to the following colour code:

TABLE 11

| | | |
|---|---|---|
| 1 → 3: | white → | pale yellow |
| 4 → 6: | yellow → | tan |
| 7 → 10: | light green → | dark green |

Colour developed after stated period at 185° C.

| Composition | minutes | | | | | | | | |
|---|---|---|---|---|---|---|---|---|---|
| No. | 0 | 10 | 20 | 30 | 40 | 50 | 60 | 70 | 80 |
| 7 | 2 | 2 | 2 | 2 | 3 | 5 | 7 | 8 | 8 |
| 13 | 1 | 1 | 1 | 1 | 3 | 4 | 5 | 7 | 8 |
| 26 | 1 | 1 | 1 | 1 | 3 | 4 | 4 | 9 | 10 |
| 27 | 1 | 1 | 1 | 1 | 3 | 4 | 4 | 9 | 10 |
| 28 | 1 | 1 | 1 | 1 | 3 | 4 | 4 | 9 | 10 |
| 29 | 1 | 1 | 1 | 1 | 3 | 4 | 4 | 9 | 10 |

The results of the press test at 180° C. on these compositions are given in Table 8. The numbers in table 12 correspond to the following colour code:

TABLE 12

| | | |
|---|---|---|
| 1 → 3: | white → | pale yellow |
| 4 → 7: | yellow → | tan |
| 8: | green | |

Colour developed after stated period at 180° C.

| Composition | minutes | | | |
|---|---|---|---|---|
| No. | 5 | 10 | 20 | 30 |
| 7 | 2 | 2 | 2 | 6 |
| 13 | 1 | 2 | 3 | 5 |
| 26 | 1 | 2 | 3 | 5 |
| 27 | 1 | 1 | 2 | 5 |
| 28 | 1 | 2 | 4 | 9 |
| 29 | 1 | 2 | 4 | 9 |

EXAMPLE VIII

In this example it is shown that the compounds according to the present invention also lend themselves very well to being injection moulded.

A formulation was prepared having the following ingredients:

| | parts by weight |
|---|---|
| P.V.C. | 100 |
| inorganic filler | 2 |
| calcium stearate | 0.5 |
| wax | 0.75 |
| stabilizer | 2.0 |

The resulting product was subjected to an oven test at 185° C. The results of this oven test are given in table 13.

TABLE 13

| Compound | initial color | 1st discoloration (minutes) | degradation time (minutes) |
|---|---|---|---|
| (Bu Ac)$_2$Sn(SC$_{12}$H$_{25}$)$_2$ | brown | 5–10 | 33 |
| (Bu Ac)$_2$Sn(SCH$_2$C$^H$(OH)—CH$_2$—O—C$_6$H$_5$)$_2$ | pale yellow | 35 | 45 |
| Bu Ac Sn(S—CH$_2$C$^H$(OH)—CH$_2$O—C$_6$H$_5$)$_3$ | pale yellow | 27 | 27 |

What is claimed is:

1. An organotin compound of the formula:

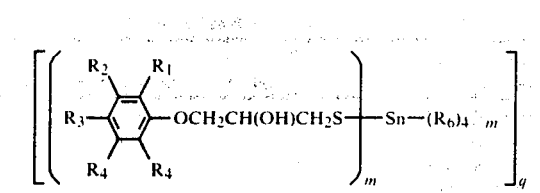

wherein q is 1 or 2; m is 1, 2 or 3; $R_6$ is an alkyl group having from 1 to 18 carbon atoms, a cycloalkyl group having from 3 to 6 carbon atoms, an aryl group, an aralkyl group, an alkaryl group having up to 30 carbon atoms or a group of the formula:

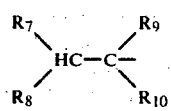

wherein $R_7$, $R_8$, $R_9$ and $R_{10}$ are each independently an alkyl group having from 1 to 18 carbon atoms, an oxygen-containing hydrocarbon group or a hydrogen atom, with the proviso that at least one of $R_7$ and $R_8$ contains, adjacent to the HC grouping, a carbonyl group which forms part of an acid group, an ester group, an acid halide group, a ketone group or an aldehyde group; when q=1, $R_1$, $R_2$, $R_3$, $R_4$ and $R_5$, are, each independently, a hydrogen atom, an alkyl or alkoxy group having from 1 to 14 carbon atoms, a cycloalkyl or cycloalkoxy group, having from 3 to 6 carbon atoms, a nitro group or a halogen atom; and when q=2, m=1, and the two structural units in the para position are interlinked, directly or by way of an oxygen atom, a methylene group, an SO$_2$ group or an isopropylidene group, and $R_1$, $R_2$, $R_4$ and $R_5$ are each as defined above.

2. A compound as claimed in claim 1 wherein $R_6$ is a group of the formula $R_{11}$OCOCH$_2$CH$_2$—, wherein $R_{11}$ is an alkyl group having from 1 to 18 carbon atoms.

3. A stabilizer composition containing a stabilizing amount of a compound of the formula of claim 1, a mono-alkyltin sulphide, a dialkyltin sulphide, a monoester tin sulphide or a diester tin sulphide.

4. The stabilizer composition of claim 3, wherein the monoalkyltin sulphide is monobutyltin sulphide.

5. A stabilized composition of a vinyl chloride based polymer and a stabilizing amount of an organotin compound of the formula of claim 1, the stabilizing composition being present in an amount of from 0.1 to 5 percent by weight of the vinyl chloride based polymer.

6. Shaped articles comprising the stabilized composition of a vinyl chloride based polymer of claim 5.

7. A process of preparing an organotin compound as claimed in claim 1, which comprises reacting a compound of the formula:

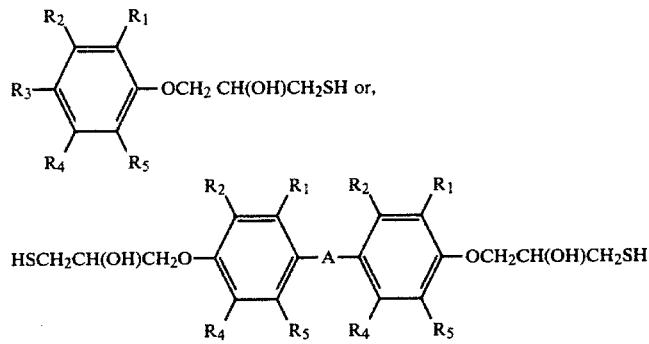

wherein $R_1$, $R_2$, $R_4$ and $R_5$ are as defined in claim 1, $R_3$ is a hydrogen atom, an alkyl or alkoxy group having from 1 to 14 carbon atoms, a cycloalkyl or cycloalkoxy group having from 3 to 6 carbon atoms, a nitro group or a halogen atom, and A represents a direct link or an oxygen atom, a methylene group, an $SO_2$ group or an isopropylidene group, with an organotin oxide or chloride having at least one group of the formula $R_6$ as defined in claim 1 bonded to tin, at a temperature of from 10° to 180° C.

8. A composition of matter comprising a vinyl chloride polymer and a stabilizing amount of an organotin compound of the formula of claim 1.

9. The composition of matter of claim 8 comprising a synergistic mixture of a compound of the formula $R_6Sn(MAP)_3$, and a compound of the formula $(R_6)Sn(MAP)_2$, wherein MAP represents a group of the formula:

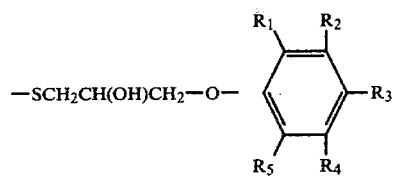

wherein $R_1$, $R_2$, $R_3$, $R_4$, $R_5$ and $R_6$ are each as defined in claim 1.

10. The stabilizer composition of claim 8 containing from 5% to 15% by weight, based on the weight of the compound having the formula of claim 1, of a phenolic antioxidant.

* * * * *